United States Patent
Myyrylainen et al.

(10) Patent No.: US 10,810,787 B2
(45) Date of Patent: Oct. 20, 2020

(54) METHOD, APPARATUS AND COMPUTER PROGRAM FOR OBTAINING IMAGES

(71) Applicant: Nokia Technologies Oy, Espoo (FI)

(72) Inventors: Lea Myyrylainen, Espoo (FI); Vuokko Tuulikki Lantz, Vantaa (FI)

(73) Assignee: Nokia Technologies Oy, Espoo (FI)

( * ) Notice: Subject to any disclaimer, the term of this patent is extended or adjusted under 35 U.S.C. 154(b) by 0 days.

(21) Appl. No.: 15/425,261

(22) Filed: Feb. 6, 2017

(65) Prior Publication Data

US 2017/0228924 A1 Aug. 10, 2017

(30) Foreign Application Priority Data

Feb. 8, 2016 (EP) .................... 16154608

(51) Int. Cl.
*G06T 15/20* (2011.01)
*G06T 7/33* (2017.01)
(Continued)

(52) U.S. Cl.
CPC .............. *G06T 15/20* (2013.01); *A61B 1/043* (2013.01); *A61B 1/24* (2013.01); *A61B 5/0086* (2013.01); *A61B 5/0088* (2013.01); *A61B 6/14* (2013.01); *A61B 6/5247* (2013.01); *A61B 8/0875* (2013.01); *A61B 8/5261* (2013.01); *G06T 7/0012* (2013.01); *G06T 7/33* (2017.01);
(Continued)

(58) Field of Classification Search
CPC ......... G06T 7/00; G06T 11/00; G06T 11/003; G06T 11/006; G06T 15/00; G06T 19/00; G06T 2207/10081; G06T 2207/10116; G06T 2207/10064; G06T 2207/30004; G06T 2207/30036; G06T 7/0012; G06T 7/33; G06T 7/70; G06T 11/60; G06T 15/20; G06T 2207/30204; A61B 1/043; A61B 1/24; A61B 5/0086; A61B 5/0088; A61B 6/14; A61B 6/5247; A61B 8/0875; A61B 8/5261; A61B 2090/365; A61B 2090/367; A61B 2090/373; A61B 2090/376; A61B 2090/378
USPC ......................................................... 345/419
See application file for complete search history.

(56) References Cited

U.S. PATENT DOCUMENTS

| | | | | |
|---|---|---|---|---|
| 5,372,502 A | * | 12/1994 | Massen | A61C 13/0004 |
| | | | | 433/215 |
| 2003/0181809 A1 | * | 9/2003 | Hall | A61B 6/12 |
| | | | | 600/425 |

(Continued)

OTHER PUBLICATIONS

"VistaCam iX—One Camera, Many Options", Durr dental, Retrieved on Mar. 31, 2017, Webpage available at : https://www.duerrdental.com/en/products/imaging/vistacam-intraoral-camera-systems/vistacam-ix/.

(Continued)

*Primary Examiner* — Sae Won Yoon
(74) *Attorney, Agent, or Firm* — Harrington & Smith (57) ABSTRACT

A method, apparatus and computer program wherein the method comprises: obtaining a three dimensional image of an object; obtaining a two dimensional image of at least a part of the object; mapping the two dimensional image onto the three dimensional image to identify the location of the part of the object in the two dimensional image within the three dimensional image; and enabling an indication of the identified location within the three dimensional image to be provided to a user.

12 Claims, 7 Drawing Sheets

(51) Int. Cl.
  *G06T 7/70* (2017.01)
  *A61B 1/04* (2006.01)
  *A61B 1/24* (2006.01)
  *A61B 5/00* (2006.01)
  *A61B 6/14* (2006.01)
  *A61B 6/00* (2006.01)
  *A61B 8/08* (2006.01)
  *G06T 7/00* (2017.01)
  *G06T 11/60* (2006.01)
  *A61B 90/00* (2016.01)

(52) U.S. Cl.
  CPC ............... *G06T 7/70* (2017.01); *G06T 11/60* (2013.01); *A61B 2090/365* (2016.02); *A61B 2090/367* (2016.02); *A61B 2090/373* (2016.02); *A61B 2090/376* (2016.02); *A61B 2090/378* (2016.02); *G06T 2207/30036* (2013.01); *G06T 2207/30204* (2013.01)

(56) References Cited

U.S. PATENT DOCUMENTS

| | | | |
|---|---|---|---|
| 2003/0220561 A1 | 11/2003 | Camus et al. | |
| 2005/0089205 A1* | 4/2005 | Kapur | A61B 6/4233 382/128 |
| 2005/0203373 A1* | 9/2005 | Boese | A61B 6/481 600/407 |
| 2007/0127803 A1* | 6/2007 | Yoshida | G06K 9/00 382/131 |
| 2008/0147086 A1* | 6/2008 | Pfister | A61B 90/36 606/130 |
| 2009/0082660 A1 | 3/2009 | Rahn et al. | |
| 2010/0094124 A1* | 4/2010 | Schoonenberg | A61B 5/0084 600/424 |
| 2010/0232672 A1* | 9/2010 | Jandt | G06T 5/50 382/132 |
| 2012/0004529 A1* | 1/2012 | Tolkowsky | G06T 19/20 600/407 |
| 2012/0010501 A1* | 1/2012 | Cerofolini | A61B 5/055 600/427 |
| 2013/0142010 A1* | 6/2013 | Ajiki | A61B 8/14 367/7 |
| 2013/0218530 A1 | 8/2013 | Deichmann et al. | |
| 2014/0342301 A1* | 11/2014 | Fleer | A61C 5/025 433/27 |
| 2014/0355830 A1* | 12/2014 | Park | G06K 9/00228 382/103 |
| 2015/0099983 A1* | 4/2015 | Hatzilias | A61B 1/07 600/478 |
| 2015/0117737 A1* | 4/2015 | Kim | G06K 9/00536 382/131 |
| 2015/0173698 A1* | 6/2015 | Sakaguchi | A61B 6/12 378/62 |
| 2016/0012183 A1* | 1/2016 | Janevski | G06F 19/3406 705/3 |
| 2016/0012582 A1 | 1/2016 | Mauldin et al. | |
| 2016/0117823 A1* | 4/2016 | Isaacs | G06T 3/20 715/863 |
| 2016/0317107 A1* | 11/2016 | Zhou | A61B 6/547 |
| 2016/0335777 A1* | 11/2016 | Borsdorf | A61B 6/032 |
| 2017/0003401 A1* | 1/2017 | Konkle | G01T 1/2018 |
| 2017/0071713 A1* | 3/2017 | Nakai | A61B 1/247 |
| 2017/0079600 A1* | 3/2017 | Bracken | A61B 6/12 |
| 2018/0263706 A1* | 9/2018 | Averbuch | A61B 6/5247 |

OTHER PUBLICATIONS

"Endoscopy", Wikipedia, Retrieved on Mar. 31, 2017, Webpage available at : https://en.wikipedia.org/wiki/Endoscopy.

"Clinical Navigation Systems for the ENT, CMF and Neuro Surgery", Scopis Medical, Retrieved on Mar. 31, 2017, Webpage available at : http://www.scopis.com/en/.

"Scientific Publications of Clinical navigation systems for the ENT, CMF and Neuro surgery", Scopis Medical, Retrieved on Mar. 31, 2017, Webpage available at : http://www.scopis.com/en/company/publications/.

Extended European Search Report dated Aug. 16, 2016, 6 pages.

* cited by examiner

METHOD, APPARATUS AND COMPUTER PROGRAM FOR OBTAINING IMAGES

TECHNOLOGICAL FIELD

Examples of the disclosure relate to a method, apparatus and computer program for obtaining images. In particular, they relate to a method, apparatus and computer program for obtaining images from within a cavity or other location that is difficult to reach for use during work on objects within the cavity or other location that is difficult to reach.

BACKGROUND

Methods and apparatus for obtaining images from a cavity or other difficult to reach location are known. For example, methods and apparatus for obtaining images of a patient for use during medical procedures are known. It is useful to enable such methods and apparatus to be improved to make the images obtained easier and more informative for a medical practitioner or other user to use.

BRIEF SUMMARY

According to various, but not necessarily all, examples of the disclosure there may be provided a method comprising: obtaining a three dimensional image of an object; obtaining a two dimensional image of at least a part of the object; mapping the two dimensional image onto the three dimensional image to identify the location of the part of the object in the two dimensional image within the three dimensional image; and enabling an indication of the identified location within the three dimensional image to be provided to a user.

In some examples the object that is imaged may comprise part of a patient. The three dimensional image may be obtained before a medical procedure is started. The two dimensional image may be captured during the medical procedure.

In some examples mapping the two dimensional image onto the three dimensional image may comprise identifying corresponding features in both the two dimensional image and the three dimensional image.

In some examples obtaining a further two dimensional image of at least part of the object and mapping the further two dimensional image onto the three dimensional image to identify the location of the part of the object in the further two dimensional image within the three dimensional image. The method may also comprise automatically updating the indication provided to a user in response to obtaining the further two dimensional image. In some examples the further two dimensional image may comprise the same part of the object as a previous two dimensional image at a different point in time. In some examples the further two dimensional image may comprise a different part of the object to a previous two dimensional image.

In some examples the method may comprise enabling the three dimensional image and a two dimensional image to be displayed simultaneously.

In some examples the indication may comprise a marker provided in the three dimensional image.

In some examples the three dimensional image is captured using at least one of x-rays, visible light, ultrasound.

In some examples the two dimensional image is captured using at least one of; visible light infra red light, fluorescence.

According to various, but not necessarily all, examples of the disclosure there may be provided an apparatus comprising: processing circuitry; and memory circuitry including computer program code, the memory circuitry and the computer program code configured to, with the processing circuitry, enable the apparatus to perform; obtaining a three dimensional image of an object; obtaining a two dimensional image of at least a part of the object; mapping the two dimensional image onto the three dimensional image to identify the location of the part of the object in the two dimensional image within the three dimensional image; and enabling an indication of the identified location within the three dimensional image to be provided to a user.

In some examples the object that is imaged may comprise part of a patient. The three dimensional image may be obtained before a medical procedure is started. The two dimensional image may be captured during the medical procedure.

In some examples mapping the two dimensional image onto the three dimensional image may comprise identifying corresponding features in both the two dimensional image and the three dimensional image.

In some examples the memory circuitry and processing circuitry may be configured to enable obtaining a further two dimensional image of at least part of the object and mapping the further two dimensional image onto the three dimensional image to identify the location of the part of the object in the further two dimensional image within the three dimensional image. The memory circuitry and processing circuitry may be configured to enable automatically updating the indication provided to a user in response to obtaining the further two dimensional image. The further two dimensional image may comprise the same part of the object as a previous two dimensional image at a different point in time. The further two dimensional image may comprise a different part of the object to a previous two dimensional image.

In some examples the memory circuitry and processing circuitry may be configured to enable the three dimensional image and a two dimensional image to be displayed simultaneously.

In some examples the indication may comprise a marker provided in the three dimensional image.

In some examples the three dimensional image may be captured using at least one of x-rays, visible light, ultrasound.

In some examples the two dimensional image may be captured using at least one of; visible light infra red light, fluorescence.

According to various, but not necessarily all, examples of the disclosure there may be provided an electronic device comprising an apparatus as described above.

According to various, but not necessarily all, examples of the disclosure there may be provided a computer program comprising computer program instructions that, when executed by processing circuitry, enables: obtaining a three dimensional image of an object; obtaining a two dimensional image of at least a part of the object; mapping the two dimensional image onto the three dimensional image to identify the location of the part of the object in the two dimensional image within the three dimensional image; and enabling an indication of the identified location within the three dimensional image to be provided to a user.

According to various, but not necessarily all, examples of the disclosure there may be provided a computer program comprising program instructions for causing a computer to perform any of the methods described above.

According to various, but not necessarily all, examples of the disclosure there may be provided a physical entity embodying the computer program as described above.

According to various, but not necessarily all, examples of the disclosure there may be provided an electromagnetic carrier signal carrying the computer program as described above.

According to various, but not necessarily all, examples of the disclosure there may be provided examples as claimed in the appended claims.

BRIEF DESCRIPTION

For a better understanding of various examples that are useful for understanding the detailed description, reference will now be made by way of example only to the accompanying drawings in which.

DETAILED DESCRIPTION

The figures illustrate example methods and apparatus 1. The method comprises: obtaining 41 a three dimensional image 71 of an object 50; obtaining 43 a two dimensional image 61 of at least a part of the object 50; mapping 45 the two dimensional image 61 onto the three dimensional image 71 to identify the location of the part of the object 50 in the two dimensional image 61 within the three dimensional image 71; and enabling 47 an indication 75 of the identified location within the three dimensional image 71 to be provided to a user.

Examples of the disclosure provide the technical effect of enabling the part of the object 50 that is captured within a two dimensional image 61 to be indicated within the three dimensional image 71. This may enable a medical practitioner to identify the respective parts of a patient using the three dimensional image 71. This may assist the medical practitioner in carrying out a medical procedure. This may also reduce the chance of the medical practitioner carrying out a procedure on the wrong part of the patient or even the wrong patient.

The methods and apparatus 1 may be for enabling images to be analysed and displayed to a user. The images that are analysed may be captured by any suitable imaging devices. The images that are captured may comprise parts of patients and may be for use during medical procedures.

Figure 1:
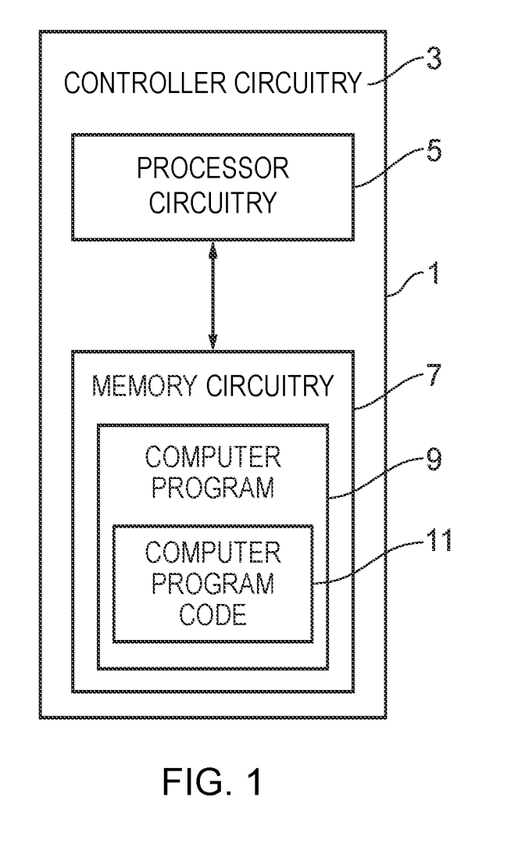
FIG. 1 illustrates an apparatus.
Figure 2:
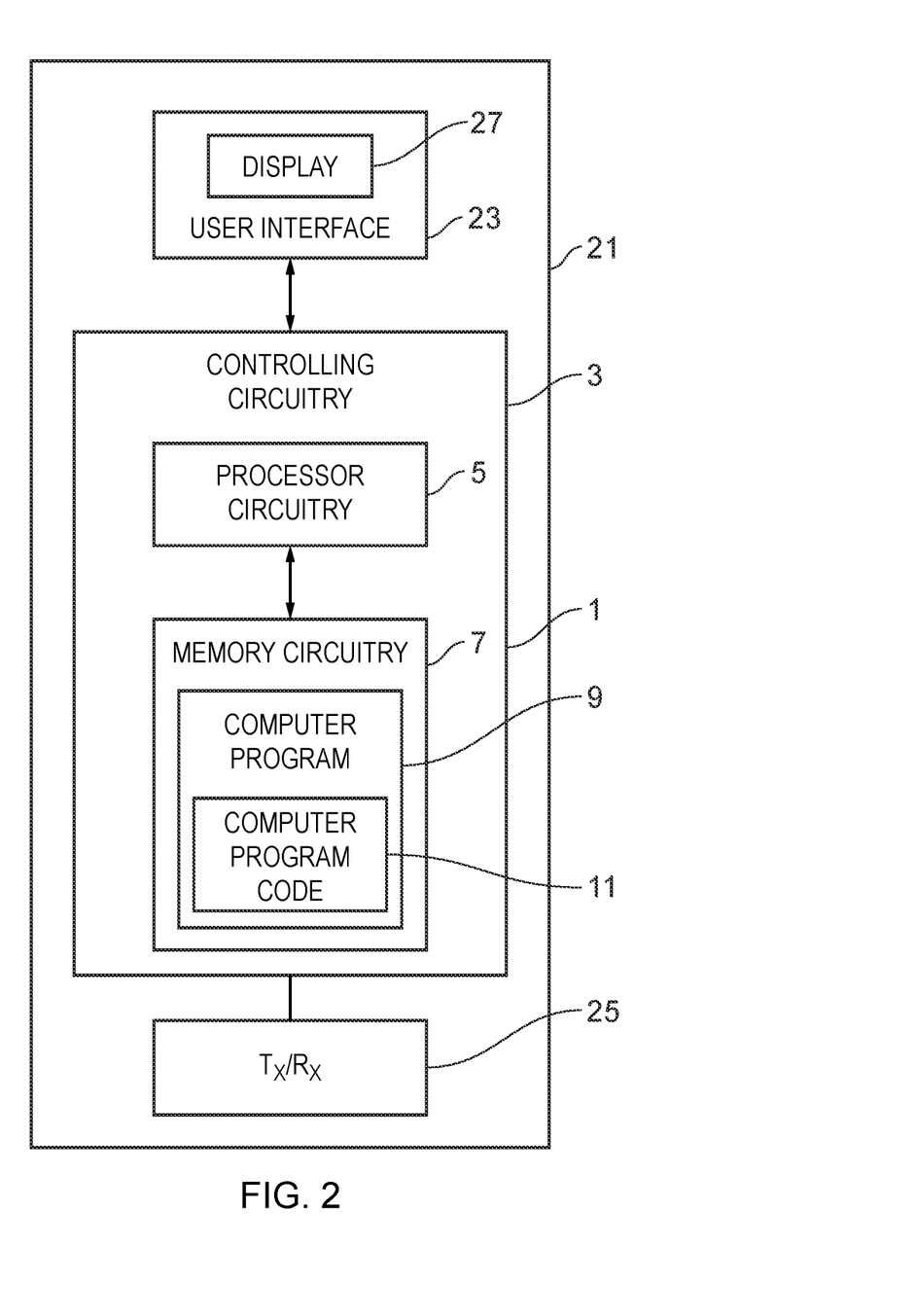
FIG. 2 illustrates an electronic device comprising an apparatus.
Figure 3:
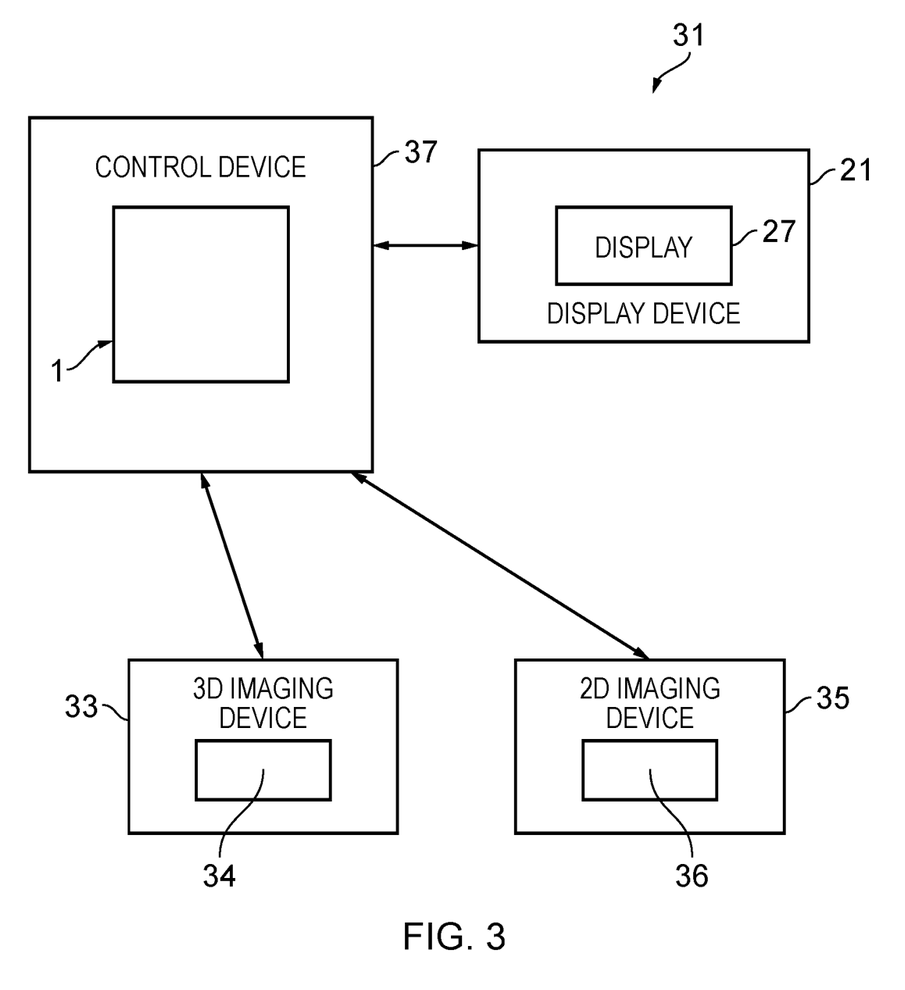
FIG. 3 illustrates a system comprising an apparatus.

FIG. 1 schematically illustrates an example apparatus 1 which may be used in examples of the disclosure. The apparatus 1 illustrated in FIG. 1 may be a chip or a chip-set. In some examples the apparatus 1 may be provided within an electronic device 21 such as a display device. An example of a display device 21 is illustrated in FIG. 2. In some examples the apparatus 1 may be provided within a system 31 which may comprise one or more imaging devices 33, 35 and one or more display devices 21. An example of such a system 31 is illustrated in FIG. 3. It is to be appreciated that the apparatus 1 may be provided in other devices and systems in other examples of the disclosure.

The example apparatus 1 comprises controlling circuitry 3. The controlling circuitry 3 may provide means for controlling an electronic device such as a display device 21 or other parts of a system 31. For instance, where the apparatus 1 is provided in a display device 21 the controlling circuitry 3 may provide means for controlling the output provided on the display 27. The controlling circuitry 3 may also provide means for performing the methods, or at least part of the methods, of examples of the disclosure.

The processing circuitry 5 may be configured to read from and write to memory circuitry 7. The processing circuitry 5 may comprise one or more processors. The processing circuitry 5 may also comprise an output interface via which data and/or commands are output by the processing circuitry 5 and an input interface via which data and/or commands are input to the processing circuitry 5.

The memory circuitry 7 may be configured to store a computer program 9 comprising computer program instructions (computer program code 11) that controls the operation of the apparatus 1 when loaded into processing circuitry 5. The computer program instructions, of the computer program 9, provide the logic and routines that enable the apparatus 1 to perform the example methods illustrated in FIG. 4. The processing circuitry 5 by reading the memory circuitry 7 is able to load and execute the computer program 9.

In some examples the computer program 9 may comprise one or more image recognition applications. The image recognition applications may be configured to identify features in a first image and find corresponding features in a second different image. In some examples of the disclosure the image recognition algorithms may be configured to indentify features in a three dimensional image and find corresponding features in a two dimensional image.

The apparatus 1 therefore comprises: processing circuitry 5; and memory circuitry 7 including computer program code 11, the memory circuitry 7 and the computer program code 11 configured to, with the processing circuitry 5, cause the apparatus 1 at least to perform: obtaining 41 a three dimensional image 71 of an object 50; obtaining 43 a two dimensional image 61 of at least a part of the object 50; mapping 45 the two dimensional image 61 onto the three dimensional image 71 to identify the location of the part of the object 50 in the two dimensional image 61 within the three dimensional image 71; and enabling 47 an indication 75 of the identified location within the three dimensional image 71 to be provided to a user.

The computer program 9 may arrive at the apparatus 1 via any suitable delivery mechanism. The delivery mechanism may be, for example, a non-transitory computer-readable storage medium, a computer program product, a memory device, a record medium such as a compact disc read-only memory (CD-ROM) or digital versatile disc (DVD), or an article of manufacture that tangibly embodies the computer program. The delivery mechanism may be a signal configured to reliably transfer the computer program 9. The apparatus 1 may propagate or transmit the computer program 9 as a computer data signal. In some examples the computer program code 11 may be transmitted to the apparatus 1 using a wireless protocol such as Bluetooth, Bluetooth Low Energy, Bluetooth Smart, 6LoWPan (IP$_v$6 over low power personal area networks) ZigBee, ANT+, near field communication (NFC), radio frequency identification, wireless local area network (wireless LAN) or any other suitable protocol.

Although the memory circuitry 7 is illustrated as a single component in the figures it is to be appreciated that it may be implemented as one or more separate components some or all of which may be integrated/removable and/or may provide permanent/semi-permanent/dynamic/cached storage.

Although the processing circuitry 5 is illustrated as a single component in the figures it is to be appreciated that it may be implemented as one or more separate components some or all of which may be integrated/removable.

References to "computer-readable storage medium", "computer program product", "tangibly embodied computer program" etc. or a "controller", "computer", "processor" etc. should be understood to encompass not only computers having different architectures such as single/multi-processor architectures, Reduced Instruction Set Computing (RISC) and sequential (Von Neumann)/parallel architectures but also specialized circuits such as field-programmable gate arrays (FPGA), application-specific integrated circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term "circuitry" refers to all of the following:

(a) hardware-only circuit implementations (such as implementations in only analog and/or digital circuitry) and (b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a mobile phone or server, to perform various functions) and (c) to circuits, such as a microprocessor(s) or a portion of a microprocessor(s), that require software or firmware for operation, even if the software or firmware is not physically present.

This definition of "circuitry" applies to all uses of this term in this application, including in any claims. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile phone or a similar integrated circuit in a server, a cellular network device, or other network device.

FIG. 2 schematically illustrates an example electronic device 21. In the example of FIG. 2 the electronic device is a display device 21. Other types of electronic device may be used in other examples of the disclosure.

The display device 21 comprises an apparatus 1 as described above. Corresponding reference numerals are used for corresponding features. In addition to the apparatus 1 the example device 21 also comprises user interface 23 and one or more transceivers 25. The user interface 23 comprises a display 27. The display device 21 may comprise other features which are not illustrated in FIG. 2 such as a power source, or any other suitable features.

The display device 21 may comprise any electronic device which may be used to enable information to be displayed to a user. In some examples the display device 21 may be a communications device. For example, the display device 21 could be a mobile telephone, tablet computer, personal computer or any other suitable device.

The apparatus 1 may be configured to obtain two dimensional images 61 and three dimensional images 71. The images 61, 71 may be obtained from one or more remote devices. The images 61, 71 may be obtained from one or more remote imaging devices 33, 35. The controlling circuitry 3 of the apparatus 1 may be configured to analyse the images 61, 71 according to examples of the disclosure and enable the images 61, 71 or at least parts of the images 61, 71 to be displayed on the display 27.

The user interface 23 may comprise any means which enables a user to interact with the display device 21. The user interface 23 may be configured to provide outputs to the user and enable a user to make user inputs.

In the example of FIG. 2 the user interface 23 comprises a display 27. The display 27 may comprise any means which may enable information to be displayed to a user. The information that is displayed on the display 27 may comprise information that is stored in the memory circuitry 7. In some examples the display 27 may be controlled by the controlling circuitry 3 to enable two dimensional and/or three dimensional images to be displayed.

The display 27 may comprise any suitable type of display 27. In some examples the display 27 may comprise a touch sensitive display 27 which may enable a users to make user inputs via the display. In some examples other types of user input devices may be provided, for instance the user input devices could comprise a key pad, gesture recognition devices or audio input devices or any other suitable input devices.

The transceiver 25 may comprise one or more transmitters and/or receivers. The transceiver 25 may enable a wireless connection between the apparatus 1 and another device. The wireless connection could be a cellular connection, a Wi-Fi connection, a Bluetooth connection or any other suitable connection.

The transceiver 25 may comprise any means which enables the display device 21 to receive information from another device. In examples of the disclosure the transceiver 25 may enable the display device 21 to obtain images which have been captured by one or more imaging devices. In some examples the transceiver 25 may enable the display device 21 to obtain a three dimensional image 71 of an object 50 from a three dimensional imaging device 33 and may enable the display device 21 to obtain a two dimensional image 61 of an object 50 from a two dimensional imaging device 35.

In some examples the transceiver 25 may also enable information to be transmitted by the display device 21. For instance in some examples the transceiver 25 may enable control information to be sent to one or more imaging devices to enable user control of the imaging device.

FIG. 3 illustrates an example system 31 comprising an apparatus 1 as described above. The system 31 comprises an apparatus 1, at least one three dimensional imaging device 33, at least one two dimensional imaging device 35, a display device 21 and a control device 37. In the example system 31 of FIG. 3 an apparatus 1 is provided within the control device 37. The apparatus 1 may be configured to perform methods according to examples of the disclosure. It is to be appreciated that the system 31 may comprise other apparatus 1 within other parts of the system 31. For instance the display device 21 may comprise an apparatus 1 which may be configured to perform at least part of the methods.

The three dimensional imaging device 33 may comprise any means which enables a three dimensional image 71 of an object 50 to be obtained. The object 50 may be part of a patient's body. The images may be obtained from inside a cavity of the patient's body. The images which are obtained may provide a three dimensional representation of an object 50 which is positioned in front of the three dimensional imaging device 33.

In some examples the images that are obtained may be for uses other than medical procedures. For instance plumbing systems may comprise pipes and cavities that may be difficult to reach. Examples of the disclosure may be used to obtain images of such locations to enable repair or maintenance work to be carried out on the plumbing system. It is to be appreciated that other examples of the disclosure may be used in any other suitable application.

The three dimensional imaging device 33 may comprise an image sensor 34 which may be configured to convert electromagnetic radiation incident on the image sensor 34 into an electrical signal to enable an image to be produced. The image sensor 34 may be arranged to detect any suitable type of electromagnetic radiation. For instance in some examples the image sensor 34 may be arranged to detect visible light or x-rays or any other suitable type of radiation. In other examples the image sensor 34 may be configured to detect other types of signals such as ultrasound instead of electromagnetic radiation. The types of images that are obtained may depend on the object 50 that is to be imaged. For instance different types of images may be used for different parts of a patient's body and/or for use in different medical procedures.

In some examples the three dimensional imaging device 33 may comprise a flexible image sensor 34 which may be arranged to capture a three dimensional image 71. In such examples the three dimensional imaging device 33 may be arranged to capture a curved image. The curved image may have less distortion than flat images. The flexible image sensor 34 may comprise a flexible polymer substrate and a graphene based sensor or any other suitable type of flexible image sensors.

In some examples the flexible image sensor 34 may be adjustable so that the shape of the image sensor 34 can be adjusted for the patient 53 or part of the patient 53 that is to be imaged. This may enable high quality three dimensional images 71 to be captured.

In some examples the three dimensional imaging device 33 may comprise a plurality of two dimensional image sensors 34. The two dimensional image sensors 34 may be rigid detectors that do not bend or flex in use. In such examples the three dimensional imaging device 33 may comprise controlling circuitry which may be configured to combine the plurality of images obtained by the two dimensional image sensors 34 to obtain a three dimensional image 71. In other examples the plurality of two dimensional images could be provided to another device, such as the control device 37, to enable controlling circuitry within the control device 37 to combine the plurality of two dimensional images to obtain the three dimensional image 71.

The three dimensional imaging device 33 may be configured to enable a three dimensional image 71 of a part of a patient 53 to be captured before a medical procedure is started. The three dimensional imaging device 33 may be configured to send images captured image to a control device 37. Once the images have been obtained by the control device the three dimensional images 71 may then be stored in memory circuitry 7 where they may be retrieved as needed.

The two dimensional imaging device 35 may comprise any means which enables a two dimensional image of an object 50 to be obtained. The object 50 may be part of a patient's body. The two dimensional imaging device 35 may be configured to obtain images of the same part of the patient's body as the three dimensional imaging device 33. The images which are obtained may provide a two dimensional representation of an object 50 which is positioned in front of the two dimensional imaging device 35.

The two dimensional imaging device 35 may comprise an image sensor 36 which may be configured to convert electromagnetic radiation incident on the image sensor 36 into an electrical signal to enable an image to be produced. The image sensor 36 may be arranged to detect visible light or any other suitable type of electromagnetic radiation or other types of signals.

In some examples the two dimensional imaging device 35 may be configured to capture images which have a smaller range than the images captured by the three dimensional imaging device 33. This means that the two dimensional imaging device 35 only captures an image of a part of the object 50 that is imaged by the three dimensional imaging device 33. For instance, the three dimensional imaging device 33 may be configured to capture an image of all of a patient's upper teeth. The two dimensional imaging device 35 might be configured to only capture an image of a small number of the patient's teeth or a part of a tooth. In some examples the two dimensional imaging device 35 may be a probe camera or any other suitable device.

The two dimensional imaging device 35 may be configured to enable a two dimensional image 61 of a part of a patient 53 to be captured during a medical procedure. The two dimensional imaging device 35 may be configured to send images captured image to a control device 37. Once the two dimensional images 61 have been obtained by the control device 37 the two dimensional images 61 may then be mapped onto three dimensional images 71 to enable the medical practitioner to identify the parts of the patient 53 that are captured in the two dimensional images 61. Any suitable methods and techniques may be used to map the two dimensional image 61 onto the three dimensional image 71.

The display device 21 may be any device which comprises a display 27. The display device 21 may be as described above in relation to FIG. 2. The display device 21 may be controlled by the control device 37 to enable one or both of the two dimensional images and three dimensional images to be provided to a user. The display device 21 may be controlled to provide an indication 75 on the three dimensional image 71 of the part of the user imaged in the two dimensional image 61.

In some examples the display device 21 may be controlled to enable the images displayed on the display 27 to be changed. In some examples the images on the display 27 may be changed automatically without any direct user input. For instance if the medical practitioner moves the two dimensional imaging device 35 this may cause the two dimensional image 61 displayed on the display 27 to change. In some examples the view of the three dimensional image 71 may also be automatically adjusted to ensure that the part of the three dimensional image 71 that is displayed comprises the same area of the patient 53 as the current two dimensional image 61. In some examples the images on the display 27 may be changed in response to a user input. For instance the medical practitioner may make a user input which causes the images on the display 27 to be changed or adjusted.

The control device 37 may comprise any means which enables control of the system 31 or parts of the system 31. The control device 37 may be a local device or a remote device. In some examples the control device 37 could be a communications device such as a tablet or mobile phone which may be located locally to the display device 21 and the imaging devices 33, 35. In such examples the control device 37 may be arranged to communicate with the display device 21 and the imaging devices 33, 35 via short range wired or wireless communication links. In other examples the control device 37 could be remote server which may enable images and other information to be stored. The remote server may enable cloud storage of information obtained by the imaging device 33, 35. In such examples the control device 37 may be arranged to communicate with the display device 21 and the imaging devices 33, 35 via long range wired or wireless communication links.

The control device 37 may be configured to obtain images from the three dimensional imaging device 33 and the two dimensional imaging device 35. The control device 37 may then enable the images obtained from the three dimensional imaging device 33 and the two dimensional imaging device 35 to be displayed by the display device 21.

In some examples the control device 37 may be configured to process the images obtained from the three dimensional imaging device 33 and the two dimensional imaging device 35 before they are displayed by the display device 21. For example the control device 37 may be configured to map the two dimensional image onto the three dimensional image to identify corresponding features within the two images. This enables the location of the part of the object 50 captured in the two dimensional image to be identified within the three dimensional image. The control device 37 may then provide information indicative of the identified location to the display device 21 to enable an indication of the identified location to be displayed to a user.

It is to be appreciated that variations of the example system 31 of FIG. 3 may be used in other examples of the disclosure. For instance in some examples the control device 37 may be used only for storage of images and the display device 21 may be used to process the images and provide indications of identified locations to the user.

Figure 4:
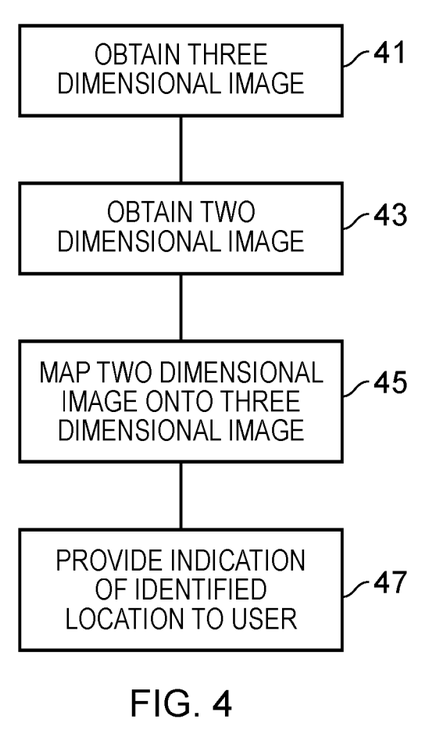
FIG. 4 illustrates a method.

FIG. 4 illustrates a method according to examples of the disclosure. The method may be implemented using apparatus 1, devices 21, 33, 35, 37 and systems 31 as described above.

The method comprises, at block 41 obtaining a three dimensional image 71 of an object 50; and at block 43 obtaining a two dimensional image 61 of at least a part of the object 50. At block 45 the method comprises mapping the two dimensional image 61 onto the three dimensional image 71 to identify the location of the part of the object 50 in the two dimensional image 61 within the three dimensional image 71 and at block 47 the method comprises enabling an indication 75 of the identified location within the three dimensional image 71 to be provided to a user.

FIGS. 5A to 7 illustrate an example method of examples of the disclosure in more detail. In the example of FIGS. 5A to 7 images of a patient's teeth 57 are captured. It is to be appreciated that other objects and other parts of a patient's body may be used in other examples of the disclosure.

Figure 5A:
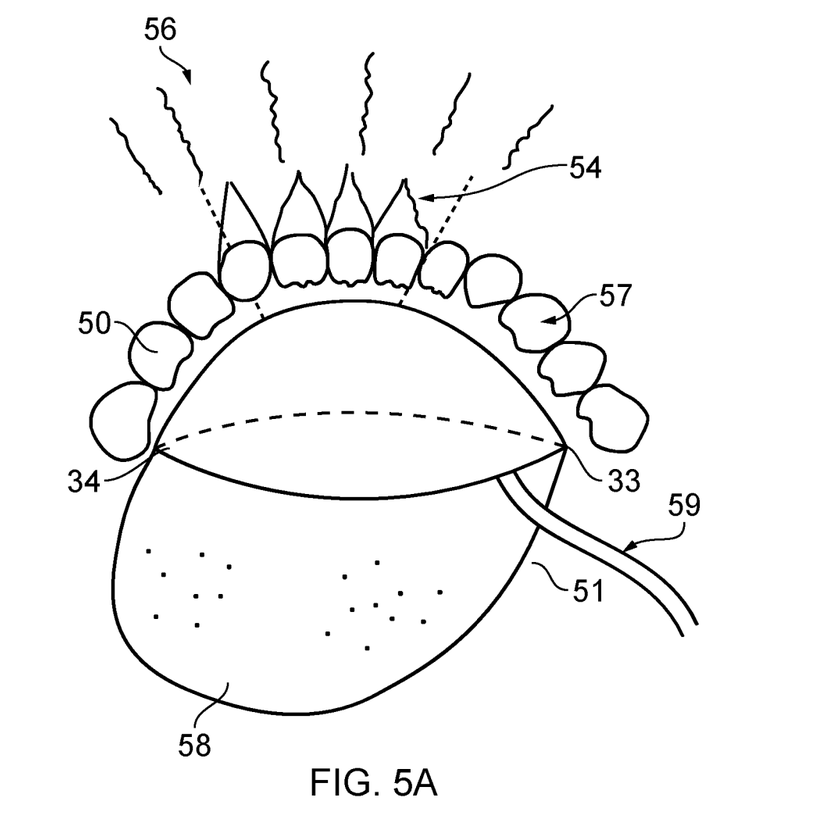
FIGS. 5A and 5B illustrate a three dimensional image being captured.
Figure 5B:
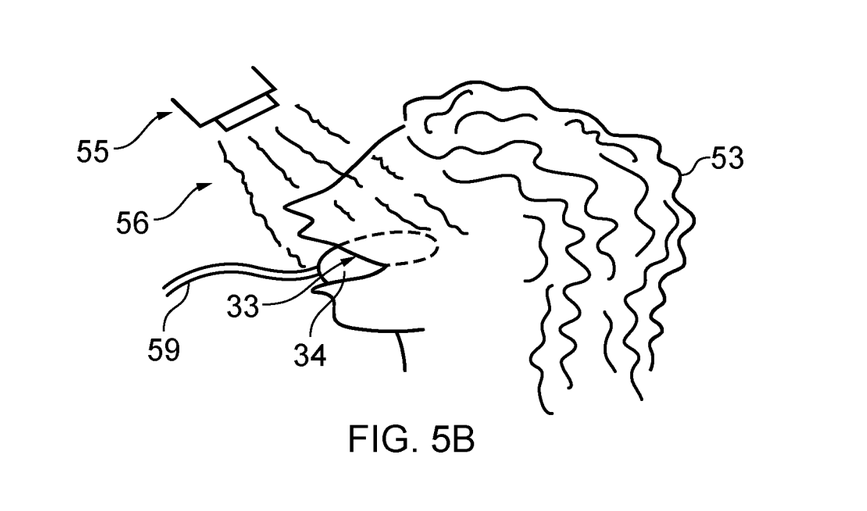

FIGS. 5A and 5B illustrate a three dimensional image 71 of an object 50 being captured. In the illustrated examples the three dimensional image 71 is captured using x-rays. Other types of three dimensional images 71 may be used in other examples of the disclosure.

In the example of FIGS. 5A and 5B the object 50 that is imaged comprises the patient's teeth 57. FIG. 5A illustrates a three dimensional imaging device 33 positioned inside of the mouth 51 of a patient 53. FIG. 5B illustrates a side view of the patient 53 while the three dimensional image is being captured.

In the illustrated example the three dimensional imaging device 33 is arranged to capture x-ray images. An x-ray source 55 is arranged to provide x-rays 56. The x-ray source 56 is positioned close to the patient 53 so that the x-rays 56 provided by the x-ray source 55 are incident on the part of the patient 53 that is to be imaged. The x-ray source 55 and the three-dimensional imaging device 33 are arranged so that the patient's teeth 57 are positioned between the x-ray source 55 and the three dimensional imaging device 33. This enables an x-ray image of the patient's teeth 57 to be captured.

As the image that is obtained is an x-ray image the three dimensional image 71 will contain information that is not visible in images obtained using visible light. For instance the three dimensional image 71 obtained in the example of FIGS. 5A and 5B will contain an image of the roots 54 of the patient's teeth 57 which are hidden below the gums as well as an image of the parts of the teeth 57 which extend above the gums.

In other examples other types of sensors might be used to obtain the three dimensional images 71. These other sensors may also obtain information that would not be shown in an image obtained using visible light. For example, if infrared radiation is used this could show an increase in temperature in parts of the patient 53 which may provide an indication of an infection or other medical condition of the patient. If fluorescent light is used this may enable caries and other infections to be identified.

In the example of FIGS. 5A and 5B the three dimensional imaging device 33 comprises a curved image sensor 34. This enables a three dimensional image 71 of the patient's teeth 57 to be obtained. In the example of FIGS. 5A and 5B the three dimensional imaging device 33 comprises a dome shaped image sensor 34. This enables a dome shaped image to be obtained. Other shaped image sensors 34 may be used in other examples of the disclosure.

The image sensor 34 is positioned inside the mouth 51 of the patient 53. The image sensor 34 may be positioned within the mouth 51 of the patient 53 so that the image sensor 34 is positioned close to the teeth 57 of the patient 53. In the illustrated examples the image sensor 34 is positioned on the patient's tongue 58. It is to be appreciated that the position of the image sensor 34 within the patient's mouth 51 may depend on the part of the mouth 51 that is to be imaged.

In the examples of FIGS. 5A and 5B the three dimensional imaging device 33 also comprises a cable 59 which is attached to the image sensor 34. The cable 59 may enable images that are captured by the image sensor 34 to be provided to a control device 37 or a display device 21 or any other suitable part of a system 31.

In some examples the three dimensional imaging device 33 may also comprise other components which are not illustrated in FIGS. 5A and 5B such as image processing circuitry. The image processing circuitry may be configured to process raw image data obtained from the image sensor 34 before it is provided to the control device 37 or the display device 21. The processing carried out by the image processing circuitry may be configured to optimize the three dimensional image 71 to facilitate the mapping of a two dimensional image 61 onto the three dimensional image 71. For instance, the processing may increase the resolution and/or contrast of features in the three dimensional image 71 that are likely to be included within a two dimensional image 61. This may reduce errors in the identification of features and the identification of corresponding features in a two dimensional image 61.

A display device 21 or other suitable device may be arranged to obtain the three dimensional images 71 captured by the three dimensional imaging device 33 and display these images to a medical practitioner. In some examples the display device 21 may enable a user to control the image that is displayed on the display 27. For instance, in some examples, the three dimensional image 71 may be rotated so that the medical practitioner can change the viewing angle of the image. In some examples the display device 21 may enable the medical practitioner to zoom in and out of the three dimensional image 71 to control the scale of the three dimensional image 71 displayed on the display 27.

The three dimensional image 71 may be captured before a medical procedure is started. Once the three dimensional image 71 has been captured it may be stored in memory circuitry 7 and then retrieved as needed by a medical practitioner. The stored image may be used during the medical procedure. Once the three dimensional image 71 has been obtained the three dimensional imaging device 33 is removed from the patient 53.

In the example of FIGS. 5A and 5B a three dimensional x-ray image of the patient's teeth 57 is obtained. The three dimensional image x-ray image can then be used during dental surgery to enable the dentist or other medical practitioner to identify features within the patient's mouth 51. The three dimensional image 71 may be used for diagnostic purposes. The three dimensional image 71 may be displayed on a display 27 during the surgery so that the dentist or other medical practitioner can refer to the image during the dental surgery.

Figure 6A:
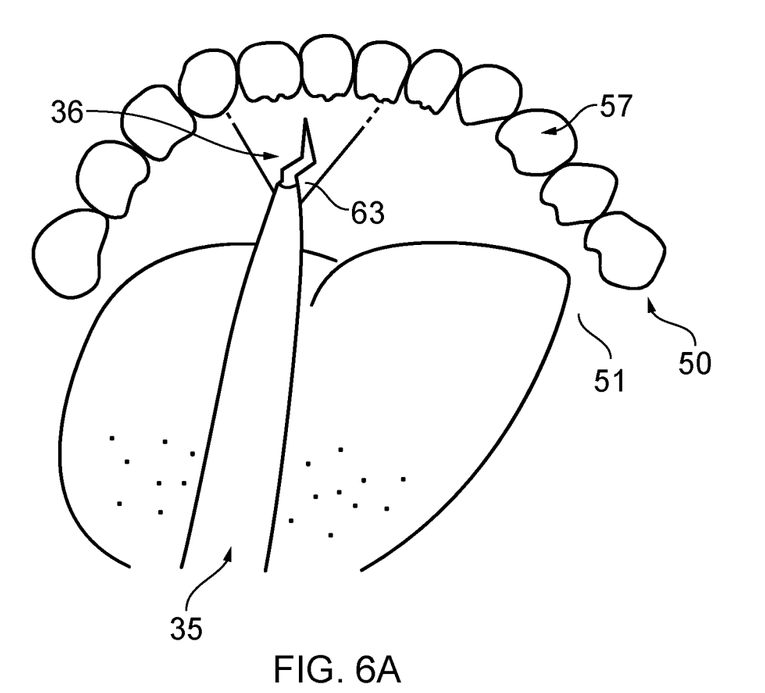
FIGS. 6A and 6B illustrate a two dimensional image being captured.
Figure 6B:
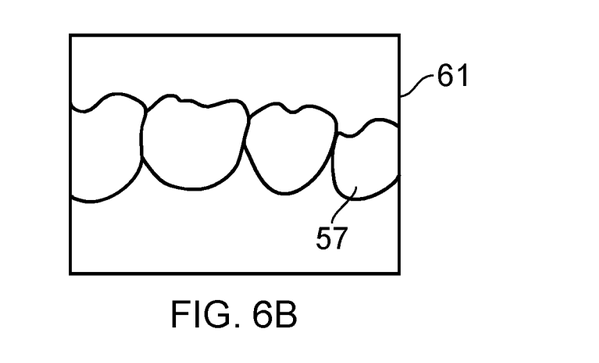

FIGS. 6A and 6B illustrate a two dimensional image 61 of an object 50 being captured. In the illustrated examples the two dimensional image 61 is captured using visible light. Other types of two dimensional images 61 may be used in other examples of the disclosure.

The object 50 that is captured in the two dimensional image 61 may be the same object 50 or at least part of the same object 50 as the object 50 that is captured in the three dimensional image 71. In the example of FIGS. 6A and 6B the object 50 that is imaged comprises the patient's teeth 57 or at least some of the patient's teeth 57.

FIG. 6A illustrates a two dimensional imaging device 35 positioned inside of the mouth 51 of a patient 53. FIG. 6B illustrates an example two dimensional image 61 that may be captured using the two dimensional imaging device 35.

In the illustrated example the two dimensional imaging device 35 is arranged to capture images using visible light. In order to enable the images to be captured the two dimensional imaging device 35 may comprise a light source. The light source may be positioned on the two dimensional imaging device 35 adjacent to an image sensor 36. This may enable the two dimensional imaging device 35 to be used to capture high quality images from inside cavities such as an oral cavity.

In the example of FIG. 6A the two dimensional imaging device 35 may be a probe device. The probe device may comprise the image sensor 34 which may be attached to a tool which is used during the dental surgery or other medical procedure. This may enable the two dimensional imaging device 35 to obtain high quality images of the area of the patient's teeth 57 that the dentist or other medical practitioner is currently working on. It is to be appreciated that similar probe device may be used for other parts of a patient's body and for other medical procedures.

In the example of FIG. 6A the two dimensional imaging device 35 is positioned inside the mouth 51 of the patient 53. As the image sensor 36 is provided within the tool being used this enables the image sensor 36, and the light source 63 to be positioned close to the teeth 57 of the patient 53.

The two dimensional imaging device 35 may be moved during the medical procedure. When the two dimensional imaging device 35 is moved this may cause a further two dimensional image 61 to be captured and provided to the control apparatus 37 or other part of the system 31. This may enable the two dimensional images 61 to be updated in real time. This may enable different parts of the patient's teeth 57 to be imaged during different stages of the medical procedure.

FIG. 6B illustrates an example two dimensional image 61 that may be obtained using the two dimensional imaging device 35. The example two dimensional image 61 comprises an image of a portion of the patient's teeth 57.

The image sensor 36 of the two dimensional imaging device 35 has a smaller range than the image sensor 34 of the three dimensional imaging device 33 so that the two dimensional imaging device 35 only captures a part of the object 50 that is to be imaged. In the example of FIGS. 6A and 6B the two dimensional image 61 only comprises four of the patient's teeth 57 while the three dimensional image 71 might comprise all of the upper portion of the patient's teeth 57.

As the two dimensional image 61 is obtained using visible light the two dimensional image 61 does not comprise some features that may be shown in the three dimensional image 71. For instance in the three dimensional image 71 the roots 54 of the patient's teeth 57 are shown. These roots 54 would not be shown in the two dimensional image 61 as they would not be visible underneath the gums of the patient 53.

In the examples of FIGS. 6A and 6B the two dimensional imaging device 35 may be arranged to enable images captured by the image sensor 36 to be provided to a control device 37 or a display device 21. In some examples the two dimensional imaging device 35 may enable video images to be provided to a control device or display device 21. This may enable the medical practitioner to view images of the patient's teeth 57 in real time as the medical procedure is being performed.

In some examples the two dimensional imaging device 35 may also comprise image processing circuitry which may be as described above. The image processing circuitry may be configured to process raw image data obtained from the image sensor 36 before it is provided to the control device 37 or the display device 21. The processing carried out by the image processing circuitry may be configured to optimize the two dimensional image 61 to facilitate the mapping of a two dimensional image onto the three dimensional image. For instance, the processing may increase the resolution and/or contrast of features in the two dimensional image 61 that are likely to be included within the three dimensional image. This may reduce errors in the identification of features and indentifying the location of the features contained in the two dimensional image 61 within the three dimensional image 71.

A display device 21 or other suitable device may be arranged to obtain the two dimensional images 61 captured by the two dimensional imaging device 35 and display these images to a medical practitioner such as dentist.

The two dimensional images 61 may be captured during a medical procedure. The two dimensional images 61 may be captured after the three dimensional images 71 have been captured. Once the two dimensional images 61 have been captured they can be mapped onto the three dimensional images to enable the location of the two dimensional images to be identified within the three dimensional image. The mapping may comprise identifying corresponding features in both the two dimensional image 61 and the three dimensional image 71. Any suitable algorithms or methods may be used to identify features within the three dimensional image 33. Corresponding features can then be identified in the two dimensional image 61 to locate the features and objects of the two dimensional image 61 within the three dimensional image 71.

The images that are obtained in the examples of FIGS. 5A to 6B may be displayed to a medical practitioner during a medical procedure. In the example of FIGS. 5A to 6B the two dimensional images 61 may be displayed on a display 27 adjacent to the three dimensional image 71 to enable the dentist to associate the region represented in the two dimensional image 61 with the region represented in the three dimensional image.

Figure 7:
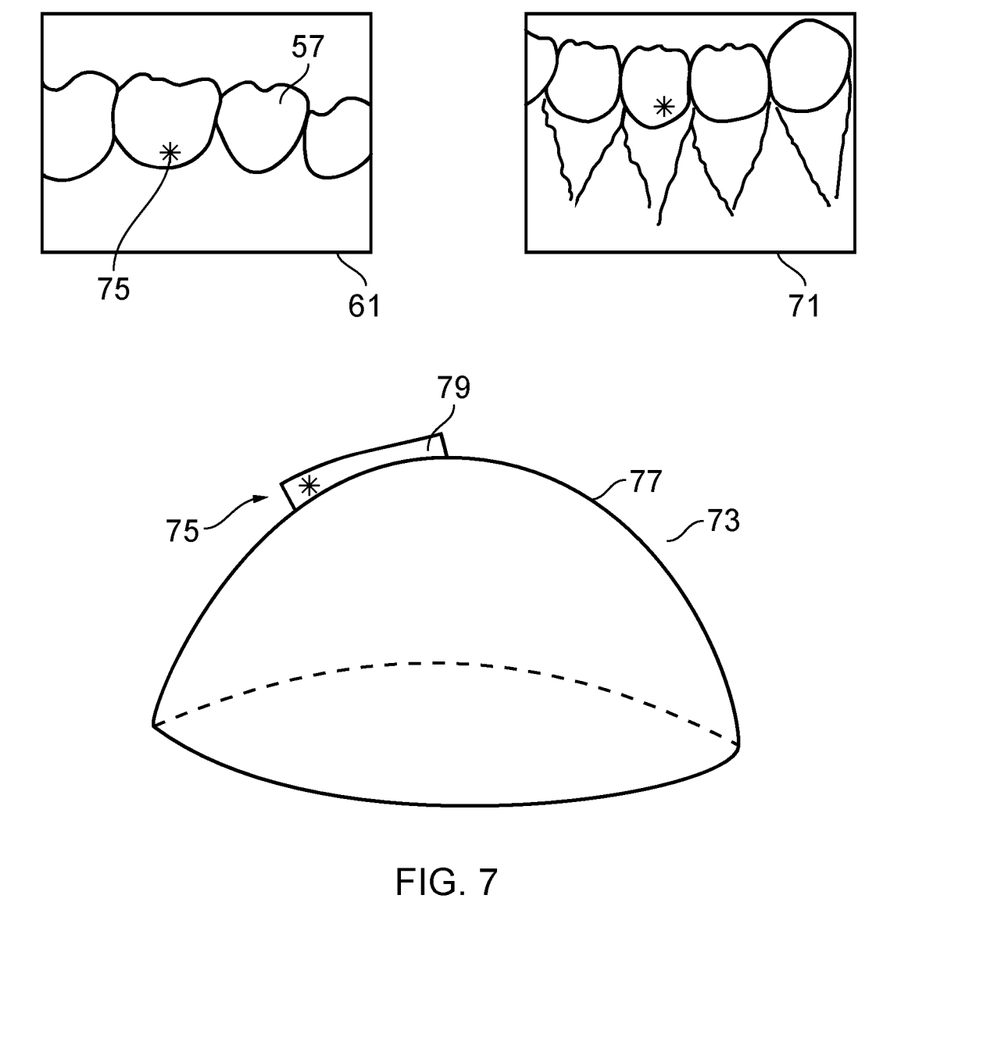
FIG. 7 illustrates the two dimensional image and the three dimensional image being provided to a user.

FIG. 7 illustrates an example arrangement of images 61, 71, 73 that may be displayed on a display 27. The images comprise a two dimensional image 61, a three dimensional image 71 and an image 73 representing the area that was captured by the three dimensional imaging device 33. In the example of FIG. 7 the three dimensional image comprises a part of the three dimensional image 71 that was obtained. In the example of FIG. 7 the part of the three dimensional image 71 that is displayed corresponds to the area covered in the two dimensional image 61. The image 73 represents the whole of the image that was captured by the three dimensional image 71.

In some examples all three of the images 61, 71, 73 may be displayed simultaneously. In other examples a user, such as a medical practitioner may select which images 61, 71, 73 or combinations of images 61, 71, 73 they would like to view.

The two dimensional image 61 may be as described above. The two dimensional image 61 comprises a representation of four of the patient's teeth 57. This may show an image of the current position of the two dimensional imaging device 35.

An indication 75 is provided in the two dimensional image 61. In the example of FIG. 7 the indication 75 comprises a star that is displayed on a portion of the two dimensional image. Other types of indication may be used in other examples of the disclosure. For instance in some examples the indication could comprise an icon other than a star. In some examples the indication could comprise a highlighted portion of the two dimensional image 61 or any other suitable type of indication.

The indication 75 may provide an indicator of the current location of the tool that is being used for the medical procedure within the patient's mouth 51. As the two dimensional images 61 may be obtained in real time this may provide the dentist or other medical practitioner with information relating to the area of the patient that they are currently operating upon.

A three dimensional image 71 may be displayed adjacent to the two dimensional image 61. In the example of FIG. 7 only a portion of the three dimensional image 71 that is captured is displayed. In the example of FIG. 7 the portion of the three dimensional image 71 that is displayed may correspond to the area of the patient 53 that is also displayed in the current two dimensional image 61. The area of the three dimensional image 71 that is to be displayed may be selected by the controlling circuitry 3. The controlling circuitry 3 may be arranged to indentify features within the two dimensional image 61 and then find these features within the three dimensional image 71. The view of the three dimensional image 71 may then be rotated and scaled so that the features displayed in the three dimensional image 71 match the features displayed in the two dimensional image 61.

The features may be identified using any suitable algorithms or image processing techniques. The features may be identified by looking for areas of high contrast or looking for patterns or other textures within the images 61, 71. For instance the identified features could comprise the outlines of teeth, gums or fillings or any other suitable features. Features which are found in both the two dimensional image 61 and the three dimensional image 71 may be identified and used to determine the area in the three dimensional image 71 that has also been captured in the two dimensional image 61. Once this area has been indentified the location of the two dimensional image 61 within the three dimensional image 71 may be used to control the images displayed on the display 27.

The processing techniques that are used to identify the corresponding features may have to account for differences in the images 61, 71 that are obtained. For instance as one image is a two dimensional image 61 and the other image is a three dimensional image 71 the representation of the objects 50 may be distorted between the two images. The image processing techniques may take into account these distortions. For instance the radius of curvature of the curved three dimensional image sensor 34 may be used to account for these distortions.

In some examples the processing techniques that are used to identify the corresponding features may have to account for different types of images 61, 71 being obtained. For instance in the current example one image is an x-ray image and the other image is obtained using visible light. This causes some features to be represented on one image that are not also represented in the other image. In some examples the image processing techniques may be configured to disregard features that are only represented in one of the images.

In some examples the display device 21 and controlling circuitry may be configured so that when the area represented in the two dimensional image 61 changes, the area displayed in the three dimensional image 71 also changes. For instance when the dentist moves the two dimensional imaging device this will change the area of the mouth 51 that is captured in the two dimensional image. The controlling circuitry 3 may determine that the features in the two dimensional image 61 have changed and may then map the features from the changed two dimensional image 61 onto the three dimensional image 71 to find the corresponding features within the three dimensional image 71. The controlling circuitry may automatically scroll through the three dimensional image 71 so that the corresponding features in the three dimensional image 71 are displayed.

As the three dimensional image 71 may be updated automatically using image recognition software or any other suitable algorithm this may make the system 31 easier for a practitioner or other user as they do not have to manually scroll through the three dimensional image 71. It is to be appreciated that in some examples the display device 21 may also enable the medical practitioner to manually change the view of the three dimensional image 71. This may enable the medical practitioner to use their preferred views as they choose.

In the example of FIG. 7 only a portion of the three dimensional image 71 that is captured is displayed. It is to be appreciated that in other examples all of the three dimensional image 71 that is captured could be displayed. In some examples the display device 21 may also enable the medical practitioner to manually change the amount of the three dimensional image 71 that is displayed. For instance display device 21 may be configured to enable the medical practitioner to zoom in and out of the three dimensional image 71.

An indication 75 is also provided in the three dimensional image 71. In the example of FIG. 7 the same indication 75 is used in both the three dimensional image 71 and the two dimensional image 61. In other examples different indications may be used in the different images.

The indication 75 provides an indicator of the current location of the sensor 36 of the two dimensional imaging device 35 within the patient's mouth 51. The location may be identified by identifying features in the two dimensional image 61 and then finding these features in the three dimensional image 71. In the example of FIG. 7 the location of the indication 75 in the two dimensional image might be indentified. The features corresponding to this location could then be identified in the three dimensional image 71. The indication 75 may then be displayed in the identified location.

In the example of FIG. 7 an image 73 representing the area that was captured by the three dimensional imaging device 33 is also displayed on the display 27. In the example of FIG. 7 the image 73 comprises a dome shape 77 which corresponds to the shape of the image sensor 34 of the three dimensional imaging device 33.

The image 73 comprises a marker 79 which indicates the area that is currently displayed in both the two dimensional image 61 and the three dimensional image 71. This marker 79 indicates to the medical practitioner the area of the patient that they are currently operating upon. This marker 79 may also enables the medical practitioner to scroll through the respective images 61, 71.

The location at which the marker 79 is displayed may be determined by identifying the area of the three dimensional image 71 that is currently displayed and then identifying the region of the sensor 34 of the three dimensional imaging device 33 that captured the currently displayed area. The marker 75 can then be displayed in the corresponding area.

In the example of FIG. 7 an indication 75 is also displayed in the image 73. The indication 75 may be the same as the indications in the two dimensional image 61 and the three dimensional image 71. The indication 75 may indicate the area that the medical practitioner is currently operating upon. This may make it easier for the medical practitioner to identify the parts of the patient that they are currently operating upon.

It is to be appreciated that when the medical practitioner moves the tool and/or the two dimensional imaging device 35 the new location of the tool and/or the two dimensional imaging device 35 may be identified and the indication 75 may be moved in the respective images 61, 71, 73 to correspond to the new, updated location of the tool and/or the two dimensional imaging device 35.

In some examples the tool and/or the two dimensional imaging device 35 might remain stationary during the medical procedure. In such examples the images obtained by the two dimensional imaging device 35 may change as the surgery progresses. For instance if the dentist removes part of a tooth 57 then this would no longer be visible in the two dimensional image 61 but would still be shown in the three dimensional image 71. In such examples features which have not been operated upon may still be used to ensure that the indications 75 and markers 79 are displayed in the correct locations.

In some examples the display 27 may be arranged to display an indication of the level of matching between the two dimensional image and the three dimensional image 71. For instance if there is a high correlation between the two dimensional image and the three dimensional image information indicating this could be displayed to provide confidence to the medical practitioner that the correct locations have been identified. If there is a low correlation then this information could also be displayed to the medical practitioner. This could provide an indication that the wrong patient or the wrong part of the patient has been identified. In some examples the level of correlation could decrease as the medical procedure is performed. For instance if the dentist is removing teeth 57 then this will reduce the matching between the two dimensional images 61 obtained after the teeth 57 have been removed and the three dimensional images 71 obtained before the teeth 57 were removed. If the level of matching decreases to a certain point the medical practitioner could obtain a new three dimensional image 71 or could remove the three dimensional image 71 from the display 27 and use just the two dimensional images 61.

Examples of the disclosure provide the advantage that they enable two dimensional images and three dimensional images to be combined so that features in one of the images can be highlighted or otherwise indicated in the other image. This may be useful in cases such as medical procedures where the two images may be used simultaneously to ensure that the medical procedures are carried out correctly.

Examples of the disclosure might reduce the risk of user error in identifying the wrong part of the patient. For instance the mapping algorithms maybe used to locate and identify specific features and may be arranged to do this to a higher accuracy than could be achieved with the human eye. This may enable the examples of the disclosure to be used to differentiate between parts of the patient that could not be achieved just by a user viewing the images.

In some examples the examples of the disclosure may ensure that the medical procedure is performed on the right part of a patient 53 or even the right patient. For instance in some examples the three dimensional image 71 might be obtained by a different medical practitioner before the medical procedure is started. The medical practitioner who is performing the medical procedure may then use the matching between the two dimensional image 61 and the stored three dimensional image 71 to ensure that they have the right patient 53 and the right part 57 of the patient 53.

The term "comprise" is used in this document with an inclusive not an exclusive meaning. That is any reference to X comprising Y indicates that X may comprise only one Y or may comprise more than one Y. If it is intended to use "comprise" with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term "example" or "for example" or "may" in the text denotes, whether explicitly stated or not, that such features or functions are present in at least the described example, whether described as an example or not, and that they can be, but are not necessarily, present in some of or all other examples. Thus "example", "for example" or "may" refers to a particular instance in a class of examples. A property of the instance can be a property of only that instance or a property of the class or a property of a sub-class of the class that includes some but not all of the instances in the class. It is therefore implicitly disclosed that a features described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. A method comprising:
   positioning a three-dimensional imaging device within an oral cavity of a dental patient;
   obtaining a three-dimensional image of teeth of the dental patient using the three-dimensional imaging device and X-rays from an X-ray source external to said oral cavity;
   storing the three-dimensional image;
   obtaining a two-dimensional image of at least one of the teeth of the dental patient using visible light from a probe-like two-dimensional imaging device inserted into the oral cavity in real time, said probe-like two-dimensional imaging device including a source of said visible light;
   mapping the two-dimensional image onto the stored three-dimensional image by identifying features in the two-dimensional image corresponding to features in the stored three-dimensional image using an image recognition algorithm;
   identifying the at least one of the teeth shown in the two-dimensional image in the stored three-dimensional image; and
   displaying the stored three-dimensional image with an indication of the at least one of the teeth shown in the two-dimensional image, said indication corresponding to a current location of the probe-like two-dimensional imaging device.

2. The method as claimed in claim 1, wherein mapping the two-dimensional image onto the stored three-dimensional image by identifying features in the two-dimensional image corresponding to features in the stored three-dimensional image using an image recognition algorithm includes identifying corresponding features in both the two-dimensional image and the stored three-dimensional image.

3. The method as claimed in claim 1, further comprising:
   obtaining a further two-dimensional image of at least one of the teeth of the dental patient;
   mapping the further two-dimensional image onto the stored three-dimensional image; and
   identifying the at least one of the teeth shown in the further two-dimensional image in the stored three-dimensional image.

4. The method as claimed in claim 3, further comprising:
   automatically updating a location of the indication in the displayed stored three-dimensional image in response to obtaining the further two-dimensional image.

5. The method as claimed in claim 1, further comprising:
   displaying the stored three-dimensional image and the two-dimensional image simultaneously.

6. The method as claimed in claim 1, wherein the indication includes a marker provided in the displayed stored three-dimensional image.

7. An apparatus comprising:
   at least one processor; and
   at least one memory including computer program code, the at least one memory and the computer program code being configured, with the at least one processor, to cause the apparatus to perform:
   obtaining a three-dimensional image of teeth of a dental patient using a three-dimensional imaging device positioned within an oral cavity of the dental patient and X-rays from an X-ray source external to said oral cavity;
   storing the three-dimensional image;
   obtaining a two-dimensional image of at least one of the teeth of the dental patient using visible light from a probe-like two-dimensional imaging device inserted into the oral cavity in real time, said probe-like two-dimensional imaging device including a source of said visible light;
   mapping the two-dimensional image onto the stored three-dimensional image by identifying features in the two-dimensional image corresponding to features in the stored three-dimensional image using an image recognition algorithm;
   identifying the at least one of the teeth shown in the two-dimensional image in the stored three-dimensional image; and
   displaying the stored three-dimensional image with an indication of the at least one of the teeth shown in the two-dimensional image, said indication corresponding to a current location of the probe-like two-dimensional imaging device.

8. The apparatus as claimed in claim 7, wherein the probe-like two-dimensional imaging device includes a second image sensor for obtaining the two-dimensional image by capturing visible light inside the cavity of a patient's body.

9. The apparatus as claimed in claim 8, wherein the second image sensor is included in the probe-like two-dimensional imaging device attached to a tool for use during dental surgery.

10. The apparatus as claimed in claim 7, wherein the three-dimensional imaging device is flexible and has an adjustable shape.

11. The apparatus as claimed in claim 7, wherein the three-dimensional imaging device captures a curved image or a dome-shaped image.

12. A computer program product comprising a non-transitory computer-readable storage medium bearing computer program code, the computer program code comprising code for performing:
   obtaining a three-dimensional image of teeth of a dental patient using a three-dimensional imaging device located positioned within an oral cavity of the dental patient and X-rays from an X-ray source external to said oral cavity;

storing the three-dimensional image;

obtaining a two-dimensional image of at least one of the teeth of the dental patient using visible light from a probe-like two-dimensional imaging device inserted into the oral cavity in real time, said probe-like two-dimensional imaging device including a source of said visible light;

mapping the two-dimensional image onto the stored three-dimensional image by identifying features in the two-dimensional image corresponding to features in the stored three-dimensional image using an image recognition algorithm;

identifying the at least one of the teeth shown in the two-dimensional image in the stored three-dimensional image; and displaying the stored three-dimensional image with an indication of the at least one of the teeth shown in the two-dimensional image, said indication corresponding to a current location of the probe-like two-dimensional imaging device.

* * * * *

UNITED STATES PATENT AND TRADEMARK OFFICE
CERTIFICATE OF CORRECTION

PATENT NO. : 10,810,787 B2
APPLICATION NO. : 15/425261
DATED : October 20, 2020
INVENTOR(S) : Lee Myyrylainen and Vuokko Tuulikki Lantz It is certified that error appears in the above-identified patent and that said Letters Patent is hereby corrected as shown below:

In the Claims

In Claim 12, Column 19, Line 1, delete "located".

Signed and Sealed this
First Day of December, 2020

Andrei Iancu
*Director of the United States Patent and Trademark Office*